United States Patent [19]
Valikai

[11] Patent Number: 5,948,014
[45] Date of Patent: Sep. 7, 1999

[54] IMPLANTABLE STIMULATION SYSTEM HAVING A SINGLE-PASS, TRIPOLAR LEAD AND PROGRAMMABLE POLARITY

[75] Inventor: Kenneth Valikai, Palos Verde Pen., Calif.

[73] Assignee: Pacesetter, Inc., Sylmar, Calif.

[21] Appl. No.: 09/012,856

[22] Filed: Jan. 23, 1998

[51] Int. Cl.⁶ .................................................. A61N 1/05
[52] U.S. Cl. ........................................... 607/123; 607/122
[58] Field of Search ..................................... 607/122, 123

[56] References Cited

U.S. PATENT DOCUMENTS

| | | |
|---|---|---|
| 3,825,015 | 7/1974 | Berkovits . |
| 3,865,118 | 2/1975 | Bures . |
| 3,903,897 | 9/1975 | Woollons et al. . |
| 3,915,174 | 10/1975 | Preston . |
| 3,949,757 | 4/1976 | Sabel . |
| 4,057,067 | 11/1977 | Lajos . |
| 4,154,247 | 5/1979 | O'Neill . |
| 4,289,144 | 9/1981 | Gilman . |
| 4,332,259 | 6/1982 | McCorkle, Jr. . |
| 4,387,717 | 6/1983 | Brownlee et al. . |
| 4,393,883 | 7/1983 | Smyth et al. . |
| 4,394,866 | 7/1983 | Hughes . |
| 4,402,329 | 9/1983 | Williams . |
| 4,458,677 | 7/1984 | McCorkle, Jr. . |
| 4,479,500 | 10/1984 | Smits . |
| 4,497,326 | 2/1985 | Curry . |
| 4,499,907 | 2/1985 | Kallok et al. ........................... 607/122 |
| 4,567,901 | 2/1986 | Harris . |
| 4,585,004 | 4/1986 | Brownlee . |
| 4,602,645 | 7/1986 | Barrington et al. . |
| 4,624,265 | 11/1986 | Grassi . |
| 4,627,439 | 12/1986 | Harris . |
| 4,643,201 | 2/1987 | Stokes . |
| 4,664,120 | 5/1987 | Hess . |
| 4,711,027 | 12/1987 | Harris . |
| 4,799,486 | 1/1989 | DuFault . |
| 4,962,767 | 10/1990 | Brownlee . |
| 5,172,694 | 12/1992 | Flammang et al. . |
| 5,304,219 | 4/1994 | Chernoff et al. . |
| 5,443,491 | 8/1995 | Snichelotto . |
| 5,522,855 | 6/1996 | Hoegnelid . |
| 5,792,194 | 8/1998 | Morra . |
| 5,800,465 | 9/1998 | Thompson et al. .......................... 607/9 |
| 5,824,029 | 10/1998 | Weijand et al. . |

OTHER PUBLICATIONS

Amplitude and Direction of Atrial Depolarization Using a Multipolar Floating Catheter: Principles for a single Lead VDD Pacing, Daniel Flammang, et al;. Angouleme General Hospical, vol. 14, pp. 1040–1048.

*Primary Examiner*—William E. Kamm
*Assistant Examiner*—Carl H. Layno

[57] ABSTRACT

A single-pass tripolar pacing/lead system for pacing and sensing electrical activity in the heart of a patient in one of a VDD or VDDR fashion. The lead system is capable of bipolar sensing of the atrium and the ventricle using a three electrode structure: a first electrode in the atrium, a second in the ventricle just below the tricuspid valve, and a third in the ventricle. The lead system also is capable of providing bipolar stimulation of the ventricle.

18 Claims, 2 Drawing Sheets

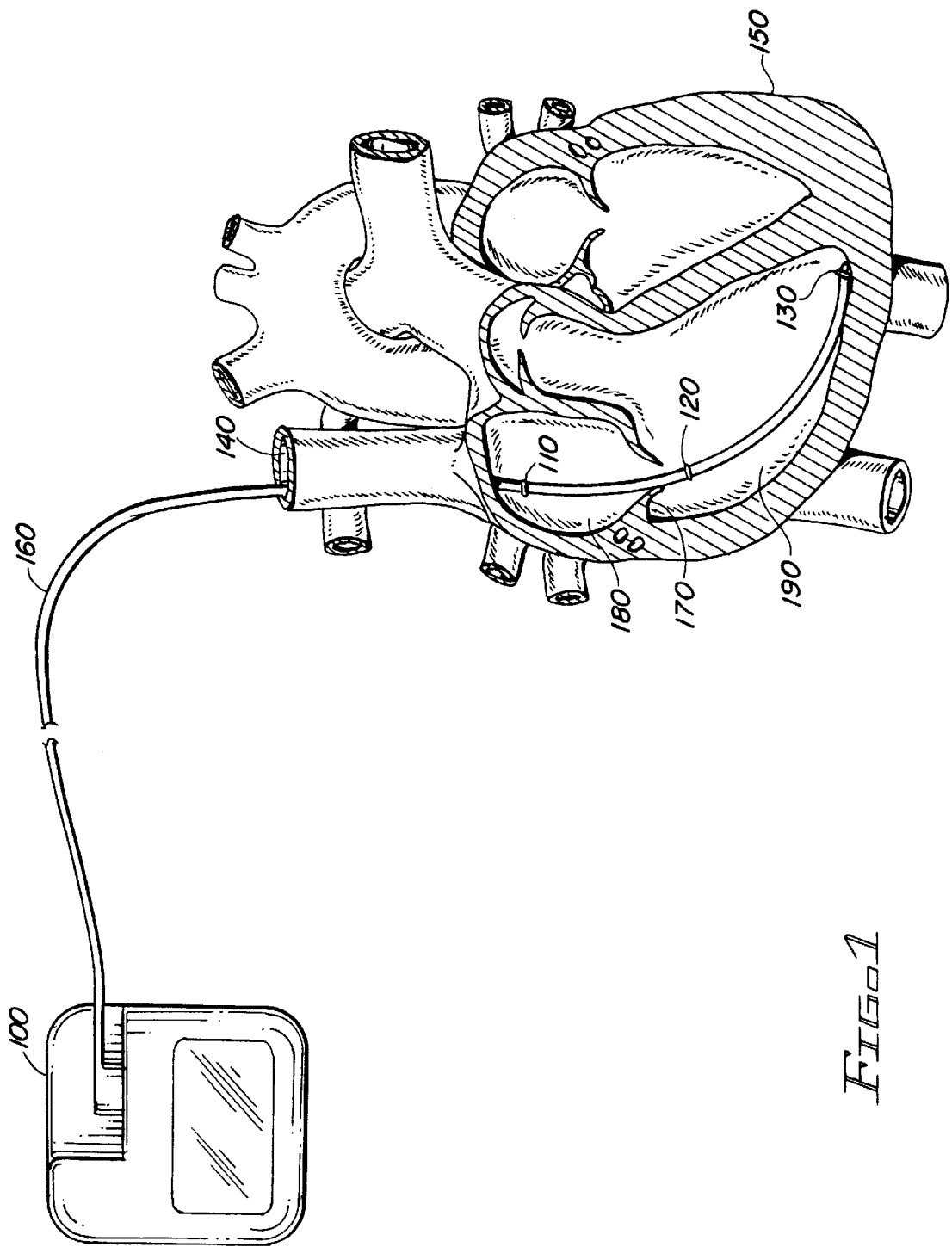

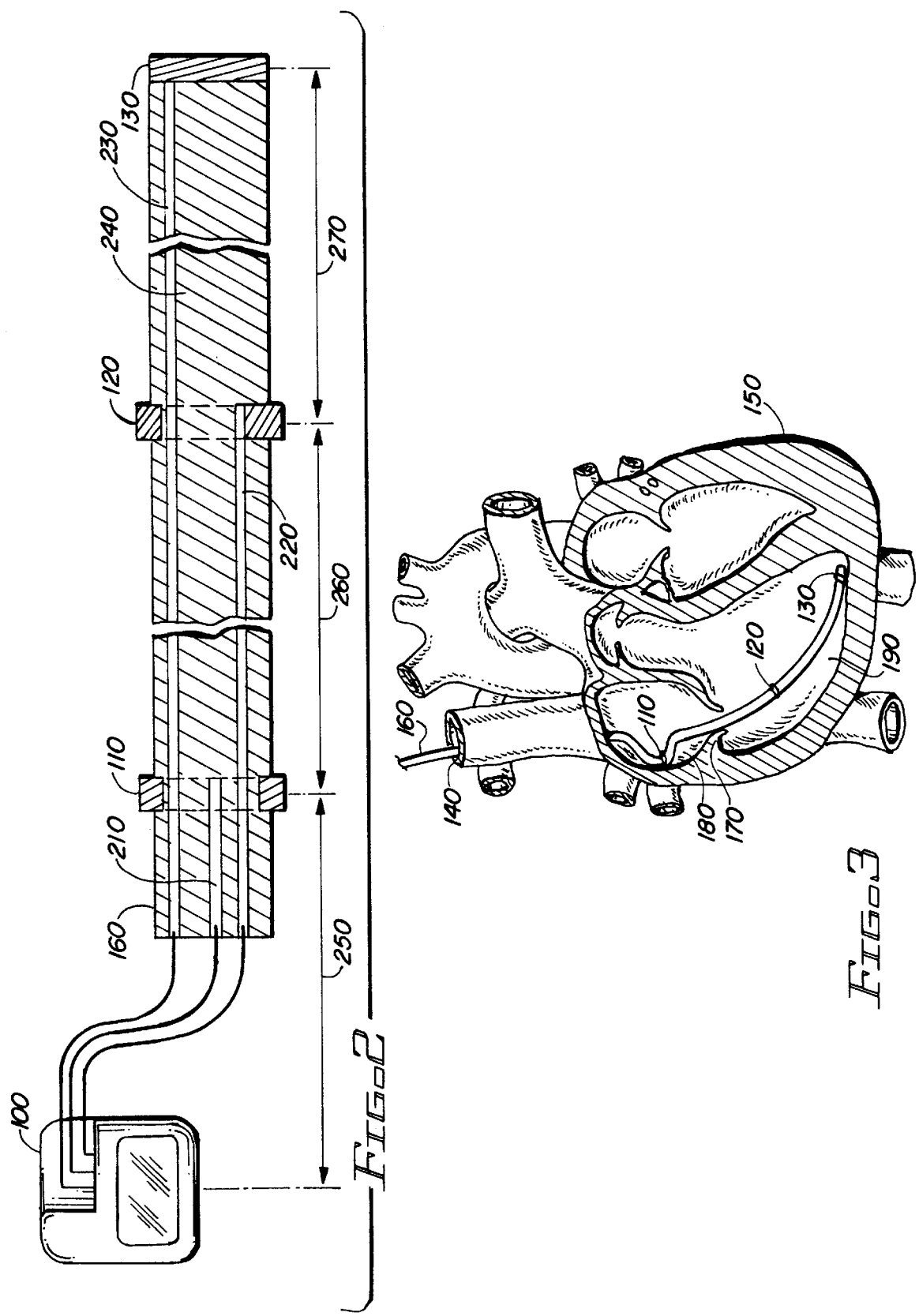

IMPLANTABLE STIMULATION SYSTEM HAVING A SINGLE-PASS, TRIPOLAR LEAD AND PROGRAMMABLE POLARITY

FIELD OF THE INVENTION

The invention generally relates to implantable stimulation devices such as cardiac pacemakers, cardioverters and defibrillators. More particularly, this invention relates to an implantable stimulation system having a single-pass, tripolar lead which delivers ventricular pacing and is capable of programmable unipolar/bipolar dual-chambered sensing.

BACKGROUND

Implantable stimulation devices, such as cardiac pacemakers, are often used to remedy improper heart function. These devices generally provide an electrical pulse to a selected area of the heart that is not (in terms of timing or strength) adequately receiving its natural pulse. Under abnormal cardiac conditions, and particularly cardiac rhythm disturbances, pacemaker therapy is applied to remedy several forms of cardiac arrhythmias (rhythm disturbances) including bradycardias, AV conduction block, supraventricular tachycardias, and atrial and ventricular ectopic arrhythmias.

There are essentially two kinds of pacemakers: single-chamber and dual-chamber. Single-chamber pacemakers are capable of sensing and pacing in only one of the atrium or the ventricle. From a practical standpoint, there are essentially two forms of single-chamber pacing: VVI (senses and paces in the ventricle) and AAI (senses and paces in the atrium).

Dual-chamber pacemakers are capable of sensing and pacing in both the atrium and the ventricle. There are many modes of dual-chamber pacing such as VDD (paces in the ventricle only, senses in the atrium and ventricle), DVI (paces in the atrium and ventricle, and senses in the ventricle only), DDI (senses and paces in both the atrium and ventricle), and DDD (senses and paces in both the atrium and ventricle, with an inhibited and triggered response to sensing).

A letter "R" is sometimes added to these pacemaker modes to indicate the pacemaker's ability to provide rate-modulated (also sometimes called rate-responsive or rate-adaptive) pacing in response to input from an independent sensor. For instance, a DDDR pacemaker is capable of adapting to the need to increase a patient's heart rate in response to physiologic stress in the absence of intrinsic response from a patient's sinus node.

A pacemaker uses a lead system to perform its sensing and stimulation functions. A lead system typically comprises at least one lead, one or more conductor coils, and one or more electrodes. The lead is the insulated wire used to connect the pulse generator of a pacemaker to the cardiac tissue. The lead carries the output stimulus from the pulse generator to the heart and, in demand modes, relays intrinsic cardiac signals back to the sensing circuitry of the pacemaker. Typically, a single-chamber pacemaker requires one lead, whereas a dual-chamber pacemaker requires two leads (one for the atrium and another for the ventricle). The conductor coil is the internal core of the pacing lead through which current flows between the pulse generator and the electrodes.

A lead may be unipolar or bipolar. A unipolar lead is a pacing lead having one electrical pole external to the pulse generator, which is usually located in the heart. The unipolar lead has one conductor coil. The electrical pole is typically a stimulating cathode (i.e., negative pole) at the distal tip of the lead. As used herein, a distal end of the lead is the end which is farther away from the pacemaker. A proximal end of the lead is the end which is connects to the pacemaker. The cathode is the electrode through which a stimulating pulse is delivered. The anode electrode (i.e., positive pole) is the case, or housing, of the pacemaker. A stimulating pulse returns to the anode using the body tissue as a return current path. A unipolar lead is relatively small in size and is theoretically more reliable than a bipolar lead. However, a unipolar lead/pacing system is more susceptible to interference by other electrical activity in a patient's body, such as inhibition due to myopotentials, and further may be prone to pectoral stimulation.

On the other hand, a bipolar lead is a pacing lead with two electrical poles that are external to the pulse generator. The bipolar lead has two conductor coils. The stimulating cathode is typically at the distal tip of the pacing lead, while the anode is an annular (i.e., ring) electrode which is few millimeters proximal to the cathode. As such, bipolar leads are less prone to pectoral stimulation. A bipolar lead has better signal-to-noise ratio than that of a unipolar lead, and thus, is less susceptible to interference from myopotential inhibition.

In practice, the cathode (i.e., stimulating) electrode is typically placed in contact with the heart tissue in order to stimulate the cardiac tissue. The anode electrode, however, does not need to be in contact with the heart tissue, since blood tends to conduct electrical currents better than the tissue itself. Nonetheless, it is preferable to have the sensing electrode in contact with the heart tissue to allow the detection of more distinct signals. For more details on bipolar lead structure and electrode placement, reference is made to U.S. Pat. No. 5,522,855, which is commonly assigned and issued to Hoegnelid on Jun. 4, 1996, and is incorporated herein in its entirety by reference. Moreover, for details on quadrapolar (four electrodes) lead structure and electrode placement, reference is made to U.S. Pat. No. 5,304,219, which is commonly assigned and issued to Chernoff et al. on Apr. 19, 1994, and is incorporated herein in its entirety by reference.

While bipolar leads are reknown for their improved sensing characteristics, some physicians still prefer unipolar leads since the additional stiffness of the bipolar leads makes them handle differently. Programmable polarity has the known advantage of permitting physicians the ability to implant the leads of choice and stock only one pacemaker model that can handle both leads. Further, if bipolar leads are initially implanted, the polarity can be modified based on the patient's needs.

There has been a long felt need to simplify the implantation of dual-chamber pacemakers by using only one lead, commonly referred to as a "single-pass" lead. The earliest known single-pass leads was a "multi-polar" device (1974) by Berkovits (U.S. Pat. No. 3,825,015,) in which two electrodes were place in the ventricle and four electrodes were placed in the atrium, however, only the best two of the four atrial electrodes were used ultimately.

"Quadrapolar" leads (1975) were attempted by Woollons et al. (U.S. Pat. No. 3,903,897) in which two electrodes were located in the apex of the ventricle and two "floating" electrodes in the atrium. However, these leads were very stiff, and positioning the atrial electrodes to make contact were difficult.

Both of these systems were extremely stiff, and either had poor contact with atrium or had extremely large, complicated connectors.

One of the simplest single-pass leads was a two-electrode lead (1979) by O'Neill (U.S. Pat. No. 4,154,247) is which electrode was placed in each of the atrium and the ventricle.

Of course, pacing thresholds were also improved upon by forcing the atrial electrode(s) to make direct contact with the cardiac tissue. This may be achieved by either pre-forming the lead in the region of the atrial electrode (as in the '247 patent, supra) or by using various anchoring or active fixation techniques by Grassi (U.S. Pat. No. 4,624,265) and Hess (U.S. Pat. No. 4,664,120).

Later, "tripolar" electrodes were developed with two electrodes in the apex of the ventricle and a single electrode in the atrium (see U.S. Pat. No. 4,585,004, Brownlee). Other attempts at tripolar electrodes included a single electrode in the ventricle, with two electrodes in the atrium (see U.S. Pat. Nos. 4,711,027, Harris; 4,962,767, Brownlee; and also 5,172,694, Flammang).

These tripolar leads of the prior art are chosen since they permit synchonicity between the atrial and ventricular chambers of the heart while providing a less stiff lead, with a smaller proximal connector (which affords a small, less complicated connector on the stimulating device) and without resorting to implanting an additional lead.

However, these prior art leads do not offer full programmability of the electrode polarity. Nor do they provide a simplified lead structure for ease of manufacture and improved reliability. Accordingly, there is a need in the cardiac pacing technology to offer a lead system which offer programmability, is compactly structured, can be easily placed in a patient's heart and, therefore, is inherently more reliable.

SUMMARY OF THE INVENTION

To overcome the above-mentioned problems, the invention provides an improved single-pass lead comprising three electrodes (tripolar) suitable for sensing intrinsic cardiac activity and stimulating cardiac tissue in a VDD fashion and having programmable unipolar or bipolar polarity.

In the preferred embodiment, one tip electrode is located at the distal end in the ventricle, one ring electrode is "floating" in the atrium, and a second ring electrode is positioned near or just below the tricuspid valve.

Ventricular pacing and sensing can occur in a unipolar fashion from the distal tip electrode to the pacemaker housing, or in a bipolar fashion from the tricuspid ring electrode to the ventricular tip electrode.

Atrial sensing can be achieved in a unipolar fashion from the atrial ring electrode to the housing, or in a bipolar fashion from the atrial ring electrode to the tricuspid ring electrode.

While the preferred embodiment is directed toward a lead suitable for VDD pacing and sensing, the present invention could be adapted to include DDD pacing and sensing if the atrial ring electrode/lead body was dimensioned so as to make contact with cardiac tissue, such as near the SA node or the atrial appendage, by pre-forming the lead in the region of the atrial ring electrode.

Advantageously, sensing of atrial and ventricular cardiac signals is enhanced, since the dipole created between the tricuspid ring electrode and either the ventricular tip electrode or the atrial ring electrode is larger (i.e., the electrodes are separated by a larger distance than standard bipolar lead arrangements). The present invention thereby detects a larger differential signal than conventional bipolar leads, is immune to myopotential signals, and still is less likely to cause pectoral stimulation.

Furthermore, the single-pass lead of the present invention adds only one additional conductor and electrode to a conventional bipolar lead, and thus is easier to implant, more reliable, and also easier to manufacture than quadrapolar or multipolar leads would be.

BRIEF DESCRIPTION OF THE DRAWINGS

The above and other aspects, features and advantages of the invention will be better understood by referring to the following detailed description, which should be read in conjunction with the accompanying drawings, in which:

FIG. 1 is a schematic diagram of one embodiment of the tripolar lead as placed in patient's heart;

FIG. 2 is a schematic diagram of the structure of the tripolar lead as implemented in FIG. 1; and FIG. 3 is a schematic diagram of another embodiment of the tripolar lead using a pre-formed lead, as placed in patient's heart.

DETAILED DESCRIPTION OF THE PREFERRED EMBODIMENT

In one embodiment, the invention provides a lead having three electrodes (tripolar) for use with an implantable stimulation device, such as a pacemaker. The tripolar lead supports bipolar pacing in the ventricle, and bipolar sensing in the atrium and ventricle of a patient's heart. This tripolar lead improves the reliability of the pacemaker operation while reducing the size of the packaging associated with the lead structure. Moreover, an in-line tripolar system reduces the size of the connector block, thereby also reducing the overall size of the implantable stimulation device.

FIG. 1 is a schematic diagram of one embodiment of the tripolar lead as placed in patient's heart. As shown in FIG. 1, a pacemaker 100 is typically implanted inside a human patient's body to sense and pace the patient's heart 150. The heart 150 includes, among other things, a right atrium 180, a right ventricle 190, a superior vena cava (SVC) 140, and a right atrioventricular (tricuspid) valve 170.

In the preferred embodiment, the lead of the invention be used with a dual chamber pacemaker, such as a VDD or VDDR pacemaker. A VDD pacemaker is one that paces in the ventricle 190, and senses in both the atrium 180 and ventricle 190. A VDDR pacemaker has characteristics similar to that of the VDD pacemaker with the added capability of rate modulation from input by an independent sensor. Rate modulation refers to the ability of the pacemaker to adjust its pacing rate in response to the patient's physical activity or metabolic demand.

A single lead 160 is typically inserted in the patient's heart 150 through the SVC 140. In the preferred embodiment, the single lead 160 comprises three electrodes: an atrial ring electrode 110, a "tricuspid" ring electrode 120, and a ventricular tip electrode 130.

The atrial ring electrode 110 is preferably positioned inferior to the SVC 140 inside the atrium 180. As noted above, the atrial ring electrode 110 does not have to be placed in contact with the heart tissue for sensing purposes.

The tricuspid ring electrode 120 is positioned just distal to (below) the tricuspid valve 170 inside the ventricle 190.

The ventricular tip electrode 130 is preferably positioned in contact with the heart tissue within the apex region inside the ventricle 190.

The lead connectors (not shown) for these electrodes preferably conform to international standard (IS-1) specifications for two of the electrodes (i.e., similar to conventional bipolar arrangements), but as yet, there is no requirement for tripolar leads.

Using a VDD (or VDDR) pacemaker, the unique lead structure and electrode placement of this invention allows bipolar pacing in the ventricle 190. During bipolar ventricular pacing (i.e., duration of a pacing spike), current flows from the ventricular tip electrode 130 to the heart tissue (i.e., myocardium) to the tricuspid ring electrode 120 to complete the current flow. Thus, in the present invention, the tricuspid ring electrode 120 is designated as the anode electrode. With the placement of the tricuspid ring electrode 120 inside the ventricle 190 (below the tricuspid valve 170), anodal stimulation to the atrium during VDD pacing is avoided.

Moreover, this single-pass lead provides bipolar sensing in the atrium 180 and ventricle 190. Hence, the tricuspid ring electrode 120 and ventricular tip electrode 130 are used as pacing and sensing electrodes in the ventricle 190. To bipolarly sense in the ventricle 190, ventricular activity is detected by measuring the differential signal between the tricuspid ring electrode 120 and ventricular tip electrode 130.

The atrial ring electrode 110 and tricuspid ring electrode 120 are used as sensing electrodes in the atrium 180. As such, atrial activity is detected by measuring the differential signal between the atrial ring electrode 110 and tricuspid ring electrode 120.

FIG. 2 is a schematic diagram of the structure of the tripolar lead as applied to the heart in FIG. 1. As shown in FIG. 2, the tripolar lead 160 comprises a first conductor 210, a second conductor 220, and a third conductor 230. These conductors are typically made of low resistance materials, such as Elgiloy, alloys of platinum-iridium, nickel-cobalt, or similar material which is well known in the art.

In one embodiment, a multifilar conductor may be employed to provide redundancy. The embodiment in FIG. 2 further illustrates a multi-lumen configuration in which each of the conductors are contained within a separate lumen within an insulation material 240. The insulation material 240 may be any electrically resistive material which prevents current flow between the conductors and body tissue. Typical lead insulation materials include silicone rubber, polyurethane, or similar matter which is well known in the art. For thinner leads, a multifilar, coaxial arrangement could be achieved if each of the conductors are mutually isolated by an insulating material, as is known in the art.

The conductors 210, 220, and 230 terminate with the atrial ring electrode 110, tricuspid ring electrode 120, and ventricular tip electrode 130, respectively. These electrodes may be made of activated carbon electrode (ACE) material, titanium nitride on titanium, platinum/iridium alloy, or similar material which is well known in the art. The atrial ring electrode 110 and tricuspid ring electrode 120 are typically annular in shape, whereas the ventricular tip electrode 130 is in a shape of a tip. The distances between the placement of these electrodes may vary from patient to patient. As a general guideline, the distance between the pacemaker and the atrial ring electrode 110 is about 38–50 centimeters (cm), and preferably about 44 cm. The distance separating the atrial ring electrode 110 and the tricuspid ring electrode 120 is about 5–10 cm, and preferably about 8 cm. The distance separating the tricuspid ring electrode 120 and the ventricular tip electrode 130 is about 3–7 cm, and preferably about 5 cm.

In an alternate embodiment, where atrial stimulation is desired, the lead body is pre-formed in the region of atrial ring electrode 110, as shown in FIG. 3, to force the atrial ring electrode to make contact with cardiac tissue and achieve lower stimulation thresholds. Pre-forming leads to get a desired placement is well known in the art. See, for example, U.S. Pat. No. 4,154,247 (O'Neill), which is hereby incorporated by reference herein.

In view of the foregoing, it will be appreciated that the present invention overcomes the long-standing need for performing VDD pacing in a bipolar fashion, with all of its inherent advantages, using a tripolar electrode. The invention may be embodied in other specific forms without departing from its spirit or essential characteristics. The described embodiment is to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An implantable single-pass lead suitable for coupling cardiac signals in a patient's atrium and ventricle to an implantable stimulation device, the lead comprising:
   a first electrode located on the lead so as to be positioned in the atrium;
   a second electrode located on the lead so as to be positioned in the ventricle in close proximity to the tricuspid valve;
   a third electrode located on the lead so as to be positioned in the apex of the ventricle;
   a lead body having a proximal connector and at least three conductors adapted to couple the first, second and third electrodes to the proximal connector, the proximal connector being adapted to make electrical contact to the implantable stimulation device;
   whereby the lead is capable of providing cardiac signals in a bipolar fashion between the first and second electrodes, and between the second and third electrodes.

2. The system as defined in claim 1, wherein the first electrode comprises a first ring electrode.

3. The system as defined in claim 1, wherein the second electrode comprises a second ring electrode.

4. The system as defined in claim 1, wherein the third electrode comprises a distal tip electrode.

5. The system as defined in claim 1, wherein:
   the first electrode comprises an atrial ring electrode;
   the second electrode comprises a tricuspid ring electrode; and
   the third electrode comprises a ventricular tip electrode.

6. The system as defined in claim 5, wherein the distance separating the atrial ring electrode and the tricuspid ring electrode is about 5–10 cm.

7. The system as defined in claim 5, wherein the distance separating the tricuspid ring electrode and ventricular tip electrode is about 3–7 cm.

8. The system as defined in claim 1, wherein:
   the lead body comprises a pre-formed region about the first electrode so as to make electrical contact with the cardiac tissue; and
   the first electrode is adapted to deliver stimulation pulses from the implantable stimulation device to the atrium.

9. An implantable stimulation system suitable for sensing cardiac signals in a patient's atrium and ventricle and stimulating at least the ventricle, the system comprising:
   a single-pass lead that includes a first electrode located on the lead so as to be positioned in the atrium, a second electrode located on the lead so as to be positioned in the ventricle in close proximity to the tricuspid valve, and a third electrode located on the lead so as to be positioned in the apex of the ventricle, the lead further having a lead body having a connector adapted to make electrical contact to the implantable stimulation device, and at least three conductors adapted to couple the first, second and third electrodes to the connector; and an implantable stimulation device having a sensing circuit that senses atrial signals and a pulse generator that triggers ventricular stimulation pulses based on the sensed atrial signals;

wherein the sensing circuit is capable of sensing atrial signals in a bipolar fashion between the first and second electrodes, and is capable of sensing ventricular signals in a bipolar fashion between the second and third electrodes.

10. The system as defined in claim 9, wherein:

the first electrode comprises an atrial ring electrode;

the second electrode comprises a tricuspid ring electrode; and the third electrode comprises a ventricular tip electrode.

11. The system as defined in claim 9, wherein the distance separating the first electrode and the second electrode is about 5–10 cm.

12. The system as defined in claim 9, wherein the distance separating the second electrode and third electrode is about 3–7 cm.

13. The system as defined in claim 9, wherein:

the lead body comprising a pre-formed region about the first electrode so as to make electrical contact with the cardiac tissue; and the pulse generator generates stimulation pulses to the first electrode based on the absence of sensed atrial signals.

14. In an implantable stimulation system, the system including an implantable stimulation device having a pulse generator for generating stimulation pulses in the ventricle, a first and second sensing circuit, each having differential inputs, for sensing cardiac signals in the atrium and the ventricle, respectively, and a case acting as a unipolar return electrode, a method of sensing one of unipolar and bipolar cardiac signals in the heart of a patient, comprising the steps of:

forming an implantable single-pass tripolar lead having an atrial electrode, a tricuspid electrode, and a ventricular electrode;

switchably coupling the differential inputs of the first sensing circuit to the atrial electrode and one of the case or the tricuspid electrode; and switchably coupling the differential inputs of the second sensing circuit to the ventricular electrode and one of the case or the tricuspid electrode.

15. The method as defined in claim 14, further comprising the step of generating bipolar stimulation pulses to the ventricle using the tricuspid electrode and ventricular electrode.

16. The method as defined in claim 14, further comprising the step of generating stimulation pulses to the atrium using the atrial electrode and the case.

17. The method as defined in claim 14, wherein the step of forming the tripolar lead comprises the step of separating the first electrode from the second electrode by a distance of about 5–10 cm.

18. The method as defined in claim 14, wherein the step of forming the tripolar lead comprises the step of separating the third electrode from the ring electrode by a distance of about 3–7 cm.

* * * * *